US008647288B2

(12) United States Patent
Jorissen

(10) Patent No.: US 8,647,288 B2
(45) Date of Patent: Feb. 11, 2014

(54) MOLDABLE INJURY THERAPY DEVICE AND METHOD

(75) Inventor: Koen Jozef Maria Jorissen, Hamburg (DE)

(73) Assignee: BSN Medical, Inc., Charlotte, NC (US)

( * ) Notice: Subject to any disclaimer, the term of this patent is extended or adjusted under 35 U.S.C. 154(b) by 522 days.

(21) Appl. No.: 12/972,681

(22) Filed: Dec. 20, 2010

(65) Prior Publication Data

US 2012/0130294 A1 May 24, 2012

Related U.S. Application Data

(60) Provisional application No. 61/416,066, filed on Nov. 22, 2010.

(51) Int. Cl.
*A61F 5/00* (2006.01)
*A61F 13/00* (2006.01)

(52) U.S. Cl.
USPC ............. 602/6; 602/5; 602/8; 602/9; 602/20; 602/21; 602/62; 602/64

(58) Field of Classification Search
USPC ............ 602/5–8, 20–22, 60–648, 9; 128/878, 128/879, 882
See application file for complete search history.

(56) References Cited

U.S. PATENT DOCUMENTS

| 4,770,299 | A | * | 9/1988 | Parker ........................... 206/409 |
| 5,520,621 | A | | 5/1996 | Edenbaum et al. |
| 5,755,678 | A | | 5/1998 | Parker et al. |
| 6,146,348 | A | * | 11/2000 | Slautterback ................... 602/21 |
| 6,730,053 | B1 | * | 5/2004 | Bodenschatz et al. .......... 602/64 |
| 6,835,182 | B2 | * | 12/2004 | Darcey ........................... 602/20 |
| 2005/0234374 | A1 | | 10/2005 | Grim et al. |
| 2007/0239093 | A1 | | 10/2007 | Wyatt et al. |

OTHER PUBLICATIONS

International Search Report and Written Opinion for PCT/US10/61521, date Feb 28, 2011.

* cited by examiner

*Primary Examiner* — Kim M Lewis
(74) *Attorney, Agent, or Firm* — Shumaker, Loop & Kendrick, LLP

(57) ABSTRACT

A multi-phase orthopedic system including a moisture-impervious sleeve, a moldable splint including a covered resin-impregnated substrate, an elongate removable wrap for retaining the splint on the limb, and a removable cast for application to the limb during a subsequent treatment phase including a cast body having an interior side and exterior side, and a flap carried by the body and movable between an open position, and a closed position overlying a part of the cast body to be applied to a treatment area of the limb, the flap adapted to cover and retain between the cast body and the flap the splint worn by the patient during the initial treatment phase in the same position as the location of the splint during the initial treatment phase. A method of immobilizing a limb in multiple treatment phases utilizing the multi-phase orthopedic system.

9 Claims, 17 Drawing Sheets

MOLDABLE INJURY THERAPY DEVICE AND METHOD

CROSS-REFERENCE TO RELATED APPLICATION

This U.S. non-provisional application claims priority to U.S. Provisional Application No. 61/416,066 filed Nov. 22, 2010 and entitled "MOLDABLE INJURY THERAPY DEVICE AND METHOD", the contents of which are incorporated by reference herein.

TECHNICAL FIELD AND BACKGROUND OF THE INVENTION

1. Field of the Invention

This invention relates to orthopaedic splint and casting products, and in particular, to an orthopaedic system that provides cost-saving, efficient and medically beneficial casting and splinting procedures in a manner not presently available. The invention also relates to a method of treating fractures, limb injuries and the like during multiple treatment phases.

2. Background of the Invention

Bone fracture treatment is a multi-phase process that includes management of the fracture in an acute phase, post-acute phase, and a later rehabilitation phase. Conventional treatments use different formats and applications with the materials constructed in different ways to offer support and comfort during the entire treatment process from acute management immediately after the injury to a substantially healed state where support is no longer required at all times.

Splinting immobilizes injured extremities and prevents further injury, decreases pain and bleeding, and allows healing to take place. There are many indications for splinting an extremity, including temporary immobilization for several orthopaedic problems other than fractures; including dislocations, injury of muscles, tendons, and ligaments, protection of vascular/nerve repairs, and postsurgical wound protection, all of which under specific circumstances may find aspects of the invention useful.

The present invention is directed to use the materials in combination in order to eliminate waste by enabling molded splinting materials used during an acute treatment stage to be retained and used during post-acute treatment and rehabilitation to ensure accurate and proper fit of the supporting structure. These procedures will ensure maximum clinical benefits by reducing misalignment and poor fitting of the splint during all phases of treatment.

The current methods of fracture support rely on medical interventions that use a series of casting and splinting regimes at various times during the process of healing and rehabilitation. This conventional methodology can often require the use of a plaster of Paris cast, followed by a synthetic cast followed by a synthetic splint to complete the repair and rehabilitation of the fracture. Each of these steps requires the patient to visit a clinic or hospital to have the existing device removed, and fitted with a new device. In other instances, particularly with severe displaced fractures and attendant severe swelling, a splint is first applied to stabilize the limb until swelling has subsided, then a cast or additional splint is applied.

The present invention involves a new and improved therapy that permits the use of the original cast in an acute phase of immobilization through to stabilization of the injury and physiotherapy.

More specifically, the present invention involves a new and improved approach to repairing a bone fracture, among other conditions, by using the original splint or cast which is fitted/molded to the anatomy for an acute phase of immobilization and then removed and fitted into a soft goods orthopaedic brace or cast for further stabilization and rehabilitation of the injury. This process ensures a correctly fitted and molded device that can be used throughout all treatment phases with minimal interference for the patient and optimum use of the materials and device.

BRIEF SUMMARY OF THE INVENTION

Therefore, it is an object of the invention to provide a fracture management system that utilizes at least some elements of the treatment device during more than one treatment phase.

It is another object of the invention to provide a fracture management system that provides improved fit between the affected limb and the fracture management device.

It is another object of the invention to provide a fracture management system that results in cost-saving, efficient and medically-efficacious casting and splinting procedures.

To achieve the foregoing and other aspects and advantages, in one embodiment a multi-phase orthopedic system is provided herein including:

(a) a sleeve formed of moisture-impervious material and sealable to prevent entry of moisture;

(b) a moldable splint positioned in the sleeve and sealed therein against entry of moisture until use, the splint comprising a substrate, a reactive system impregnated into or coated onto the substrate and remaining stable when maintained in substantially moisture-free conditions and hardening upon exposure to sufficient moisture to form a rigid, self supporting structure, and a cover enclosing the substrate along its length and forming a barrier between the substrate and a limb during an initial treatment phase during which the splint is worn by a patient on the limb;

(c) an elongate removable wrap for retaining the splint on the limb; and (d) a removable cast for application to the limb during a subsequent treatment phase, the cast including a cast body having an interior side and exterior side, and a flap carried by the body and movable between an open position, and a closed position overlying a part of the cast body to be applied to a treatment area of the limb, the flap adapted to cover and retain between the cast body and the flap the splint worn by the patient during the initial treatment phase in the same position as the location of the splint during the initial treatment phase.

In a further embodiment, the substrate is pre-formed into a shape suitable for application to a limb to be treated.

In a further embodiment, the removable cast includes a plurality of straps and complementary strap fastening rings for being releasably positioned around the cast for securing the cast to the limb.

In a further embodiment, the cast includes a padding layer positioned on the cast to overlie a part of the cast body to be applied to the treatment area of the limb.

In a further embodiment, the cast includes a short arm cast adapted for being placed on a forearm of a patient, and includes a thumb recess portion positioned for being receiving the thumb and a retention strap for retaining the thumb recess portion around the thumb.

In a further embodiment, the substrate includes an elongate medical bandage material substantially the same length as the sleeve and positioned in the sleeve in a single length along the length of the sleeve, and a seal for resealing the sleeve against entry of moisture after a predetermined length of the bandage material has been dispensed from the sleeve for use to prevent hardening of the substrate of the bandage material remaining in the sleeve.

According to another embodiment, a method of immobilizing a limb in multiple treatment phases is provided herein, including the steps of:

(a) providing:
  (i) a sleeve formed of moisture-impervious material and sealable to prevent entry of moisture;
  (ii) a splint positioned in the sleeve and sealed therein against entry of moisture until use, the splint comprising a substrate, a reactive system impregnated into or coated onto the substrate and remaining stable when maintained in substantially moisture-free conditions and hardening upon exposure to sufficient moisture to form a rigid, self supporting structure, and a cover enclosing the substrate along its length and forming a barrier between the substrate and a limb during an initial treatment phase during which the splint is worn by a patient on the limb;
  (iii) an elongate removable wrap for retaining the splint on the limb; and
  (iv) a removable cast for application to the limb, and comprising a cast body having an interior side and exterior side, and a flap carried by the body and movable between an open position, and a closed position overlying a part of the cast body to be applied to a treatment area of the limb, the flap adapted to cover and retain the splint between the cast body and the flap;

(b) removing the splint from the sleeve and wetting the splint;

(c) molding the splint to the limb;

(d) securing the splint in its molded position to the limb for being worn during an initial orthopedic treatment phase;

(e) removing the splint from the limb;

(f) placing the splint between the flap and the cast body of the cast; and (g) releasably applying the cast and the splint to the limb for being worn during a subsequent orthopedic treatment phase.

In a further embodiment, the method includes the step of pre-forming the substrate into a shape suitable for application to a limb to be treated.

In a further embodiment, the method includes the step of providing an elongate medical bandage material substantially the same length as the sleeve and positioned in the sleeve in a single length along the length of the sleeve, and a seal for resealing the sleeve against entry of moisture after a predetermined length of the bandage material has been dispensed from the sleeve for use to prevent hardening of the substrate of the bandage material remaining in the sleeve.

In a further embodiment, the method includes the step of removing the cover from the substrate before placing the splint between the flap and the cast body of the cast.

According to another embodiment, a removable cast for application to a limb during an orthopedic treatment phase is provided including:

(a) a cast body having an interior side and exterior side; and (b) a flap carried by the body and movable between an open position, and a closed position overlying a part of the cast body to be applied to a treatment area of the limb, the flap adapted to cover and retain between the cast body and the flap a splint worn by a patient during an initial treatment phase.

In a further embodiment, the cast includes a plurality of straps and complementary strap fastening rings attached to the cast body for being releasably positioned around the cast for securing the cast to the limb.

In a further embodiment, the cast includes a padding layer positioned on the cast to overlie a part of the cast body to be applied to the treatment area of the limb.

In a further embodiment, the cast includes a short arm cast adapted for being placed on a forearm of a patient, and includes a thumb recess portion positioned for being receiving the thumb and a retention strap for retaining the thumb recess portion around the thumb.

Additional features and advantages of the invention will be set forth in the detailed description which follows, and in part will be readily apparent to those skilled in the art from that description or recognized by practicing the invention as described herein.

BRIEF DESCRIPTION OF THE DRAWINGS

Some of the objects of the invention have been set forth above. Other objects and advantages of the invention will appear as the description of the invention proceeds when taken in conjunction with the following drawings, in which.

DETAILED DESCRIPTION OF THE INVENTION

The present invention will now be described more fully hereinafter with reference to the accompanying drawings in which exemplary embodiments of the invention are shown. However, the invention may be embodied in many different forms and should not be construed as limited to the representative embodiments set forth herein. The exemplary embodiments are provided so that this disclosure will be both thorough and complete, and will fully convey the scope of the invention and enable one of ordinary skill in the art to make, use and practice the invention.

The present invention has application in various types and combinations of fracture treatment methods, phases and devices. For purposes of illustration, this application describes the invention as used in a treatment process wherein a rigid splint is applied and molded to a fractured limb during an acute or post-acute phase of treatment, followed by use of the substrate portion of the splint as a support in a cast during either a post-acute or rehabilitation phase of treatment. It is understood, however, that the various elements of the invention can also be used sequentially with a plaster of Paris or synthetic cast or splint as medically required.

Figure 1:
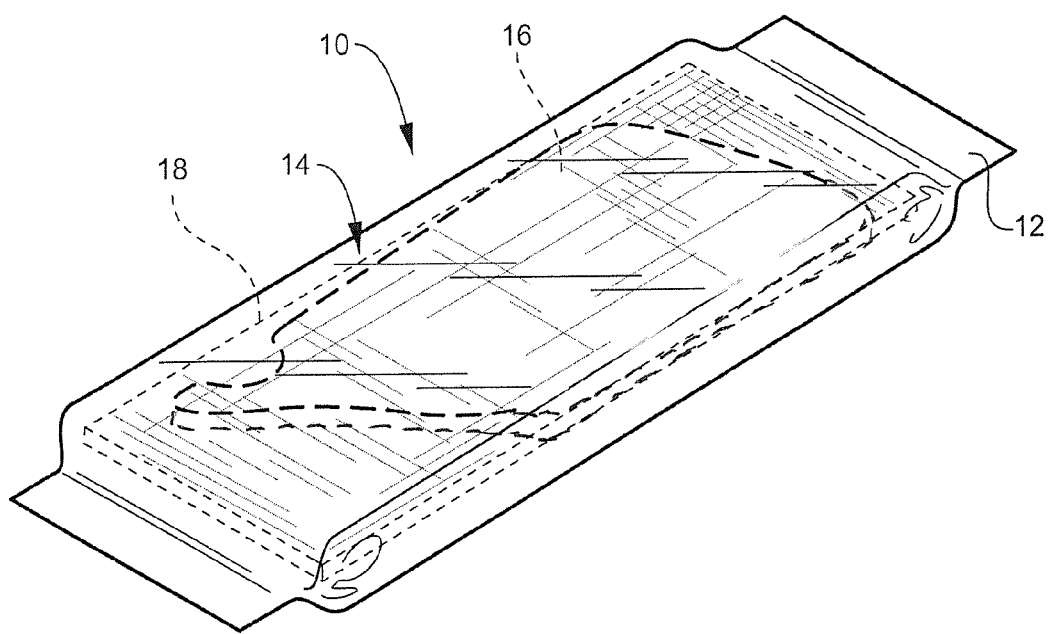
FIG. 1 is a perspective view of a precut form of splint in its storage package.
Figure 2:
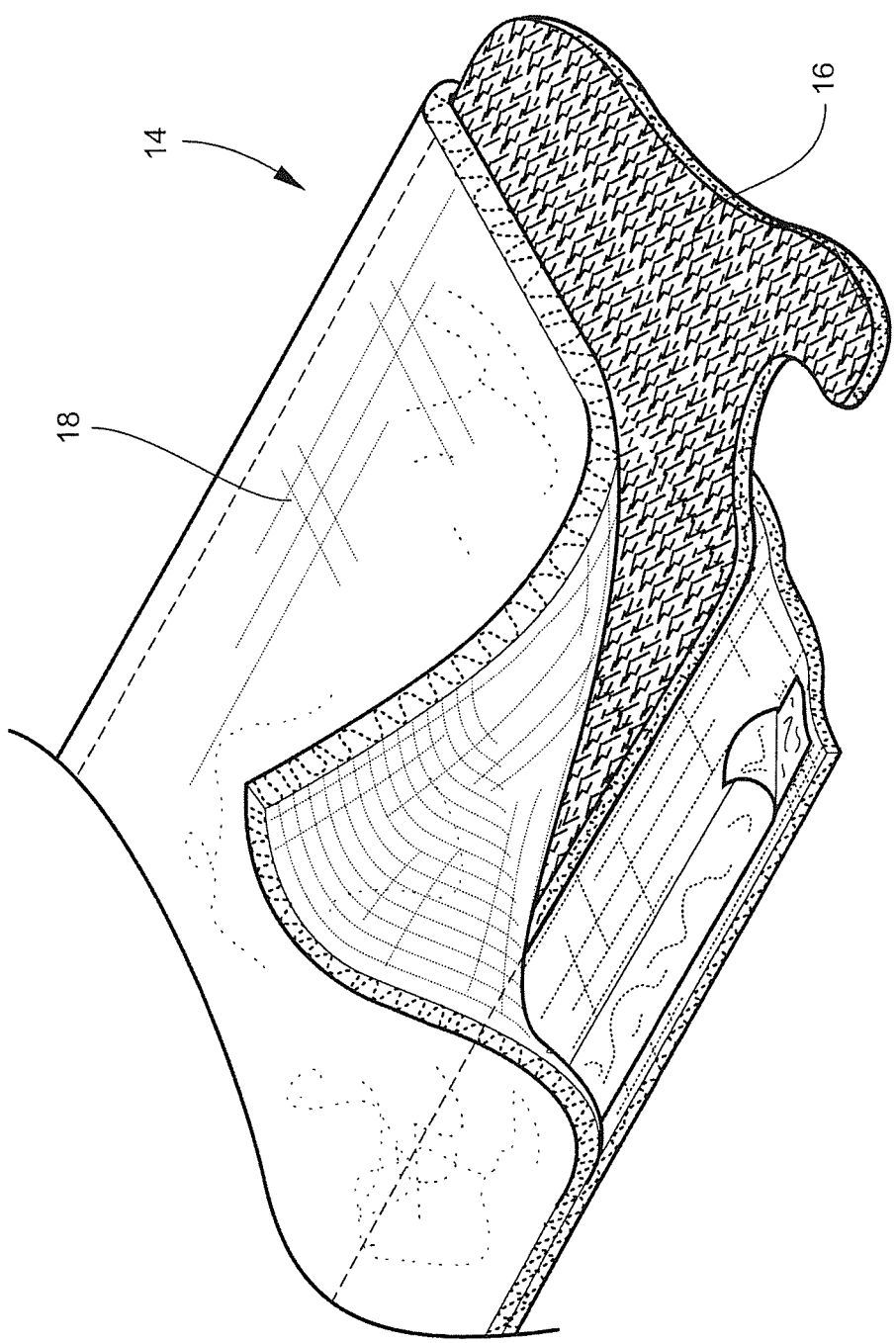
FIG. 2 is a perspective view, with a portion of the cover cut away, showing the substrate portion of the splint.
Figure 3:
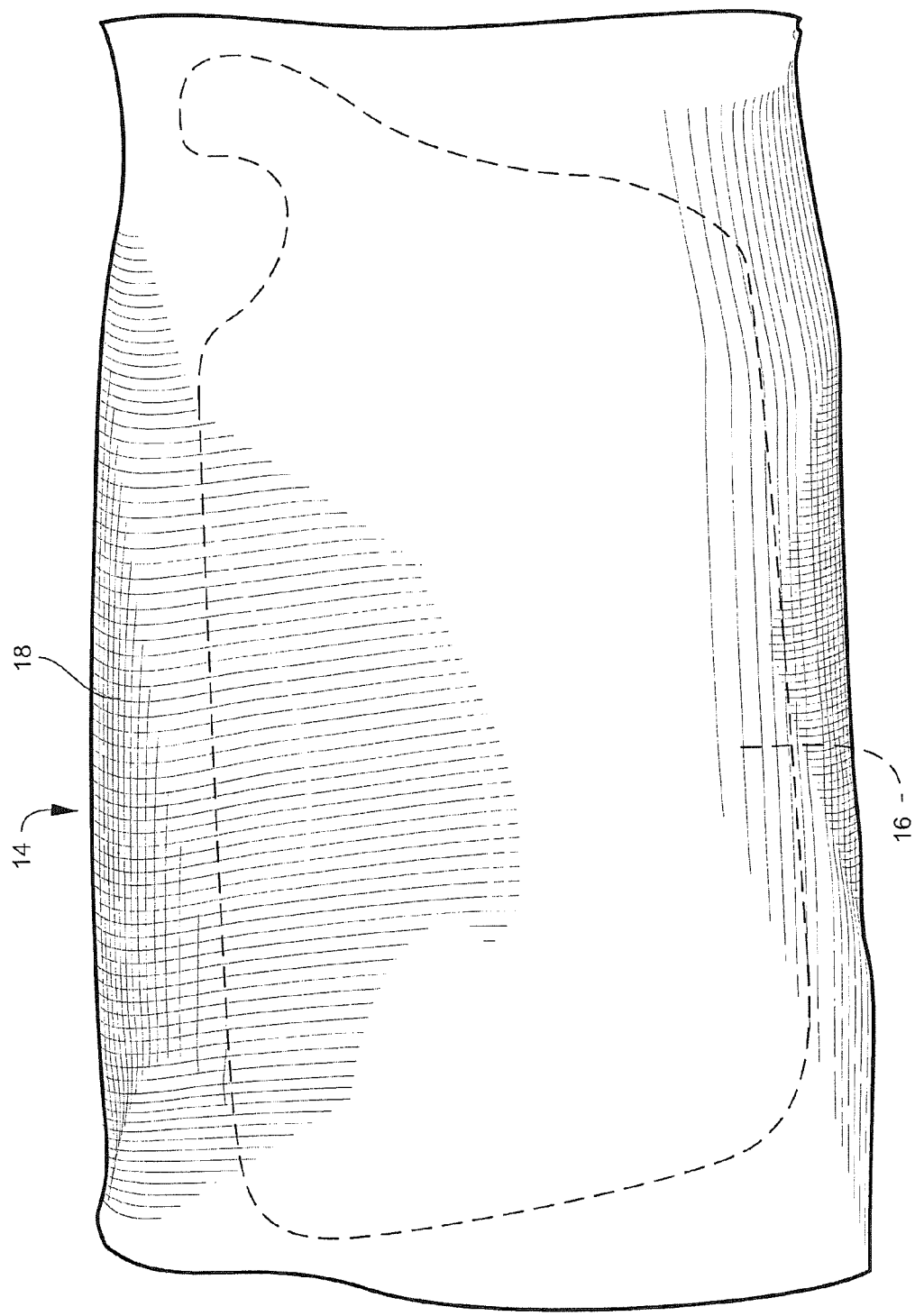
FIG. 3 is a top plan view showing the splint cover enclosing the substrate.

Referring now specifically to the drawings, FIGS. 1-3 illustrate one preferred embodiment of a splint product 10 that includes an outer water and moisture-proof envelope 12, for example, laminated plastic and foil, within which is sealed in moisture-free condition a splint 14. As best shown in FIGS. 2 and 3, the splint 14 is formed of a substrate of woven, knitted or non-woven fabric substrate 16 enclosed within an outer cover 18.

In a preferred embodiment, the substrate 16 is constructed from a non-glass spacer fabric knitted from a 455 decitex 96 filament high tenacity polyester on 5 of the knitting machine needlebars with a weight of ≥6.0 grams/denier. Other suitable synthetic fabrics, as well as fiberglass fabric, may also be used. The 6$^{th}$ needlebar is threaded using a 2-fold 167 decitex textured polyester yarn. The 6$^{th}$ bar is the middle needlebar and positions the textured polyester yarn to prevent the hardenable resin from leeching out of the fabric. The substrate 16 preferably weighs 410 grams/m$^2$, and is constructed with 32 wales and 32 courses/cm. The substrate 16 is preferably about 3 mm thick.

The substrate 16 is coated or impregnated with a moisture/water activated hardenable resin of known type such as, for example, that disclosed in applicant's U.S. Pat. No. 4,770,299. The moisture/water activated hardenable substrate 16 will become rigid in approximately 15 minutes, with strength of ≥1.6 kgf/cms. This is sufficiently rigid to stabilize a bone fracture in both animals and humans.

The cover 18 is constructed from a polypropylene monofilament 0.1 mm yarn, and the fabric is knitted on 3 of 4 knitting machine needlebars. The 4$^{th}$ bar is on the outside of the cover 18 and produces a flat polypropylene yarn, 100 denier, 72 filament, to wick the moisture away from the wearer's skin. The monofilament yarn is formed in the center of the cover 18 and acts as a drainage route for water and/or moisture. The fabric will normally dry completely in 90 minutes or less, depending on ambient temperature and humidity. The moisture vapor transmission rate for fabric of the cover 18 is 580 grams/m$^2$/24 hours.

Figure 4:
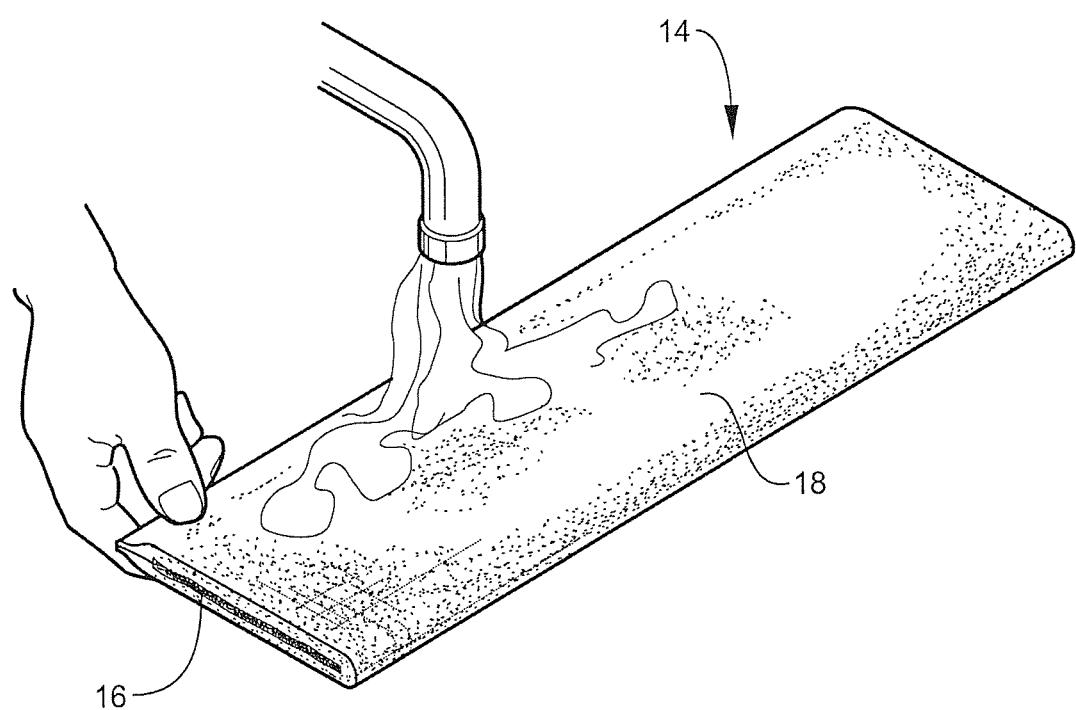
FIG. 4 illustrates wetting of the splint after removal from its storage package prior to application to the fracture site.
Figure 5:
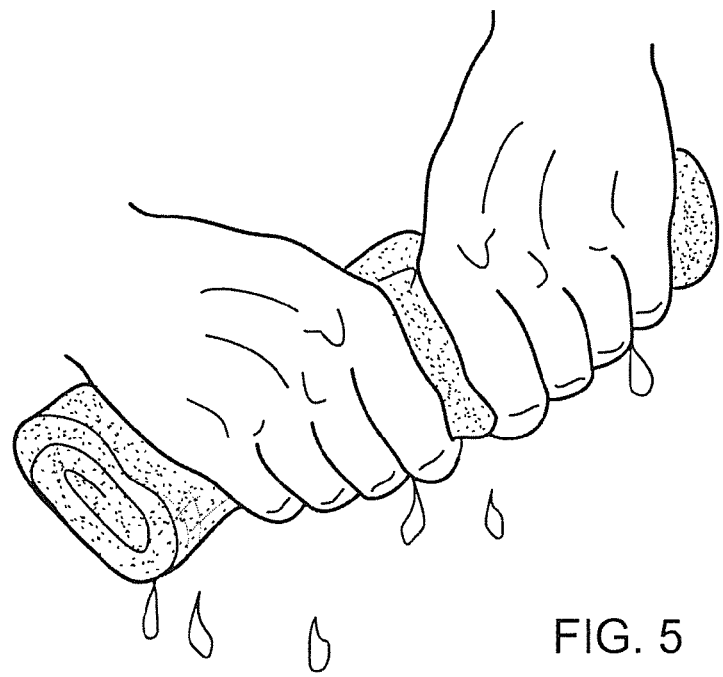
FIGS. 5 and 6 illustrate the process of removing excess moisture and smoothing the splint after wetting, respectively.
Figure 6:
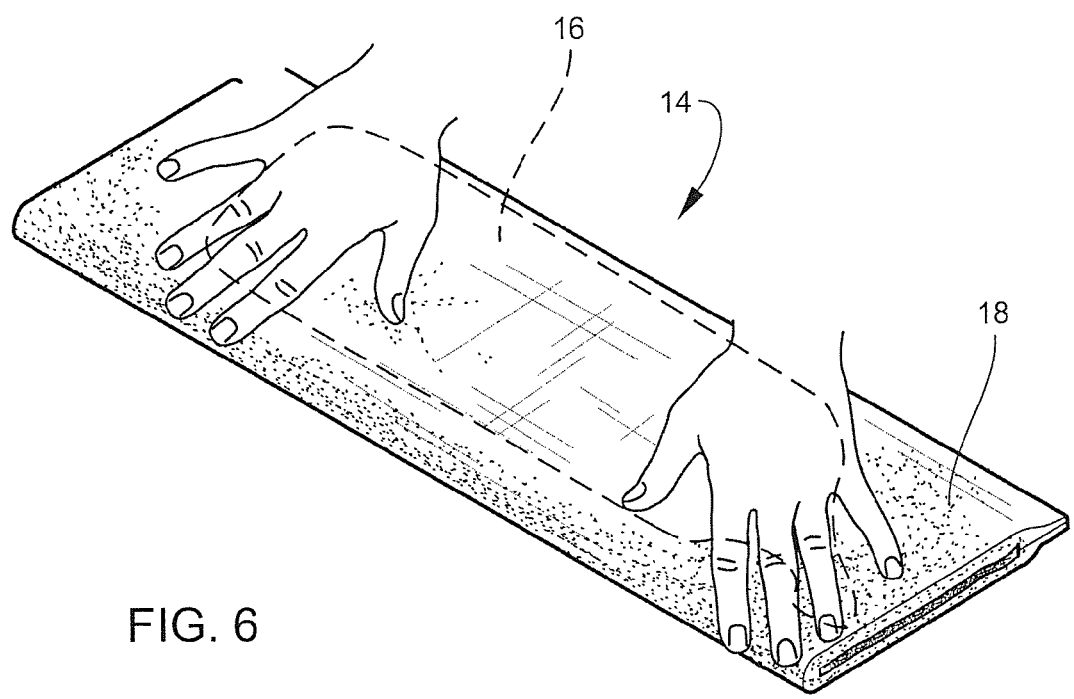

As shown in FIGS. 2 and 3, the substrate 16 is pre-cut into a shape suitable for application to a specific limb or limb part, for example an adult short arm splint, as shown. FIGS. 4, 5 and 6 illustrate a medically appropriate application technique that includes wetting the splint 14 with tepid water, FIG. 4, removing the excess water by rolling the substrate into a towel, FIG. 5, and flattening the splint 14 to prevent wrinkles when the splint 14 is applied. If desired, any excess material of the cover 18 may be trimmed.

Figure 7:
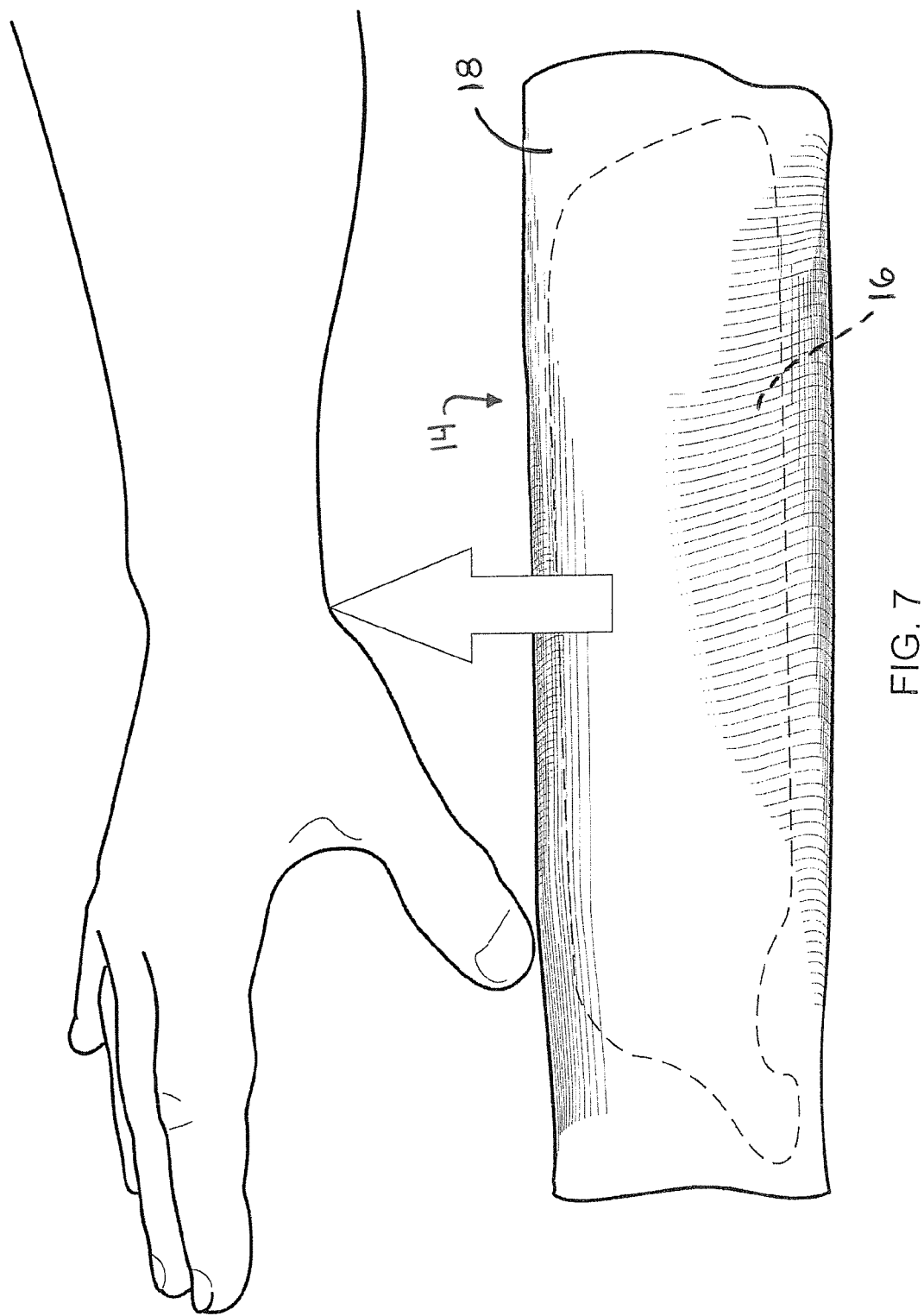
FIG. 7 shows application and molding of the splint to the medial aspect of a forearm and hand.
Figure 8:
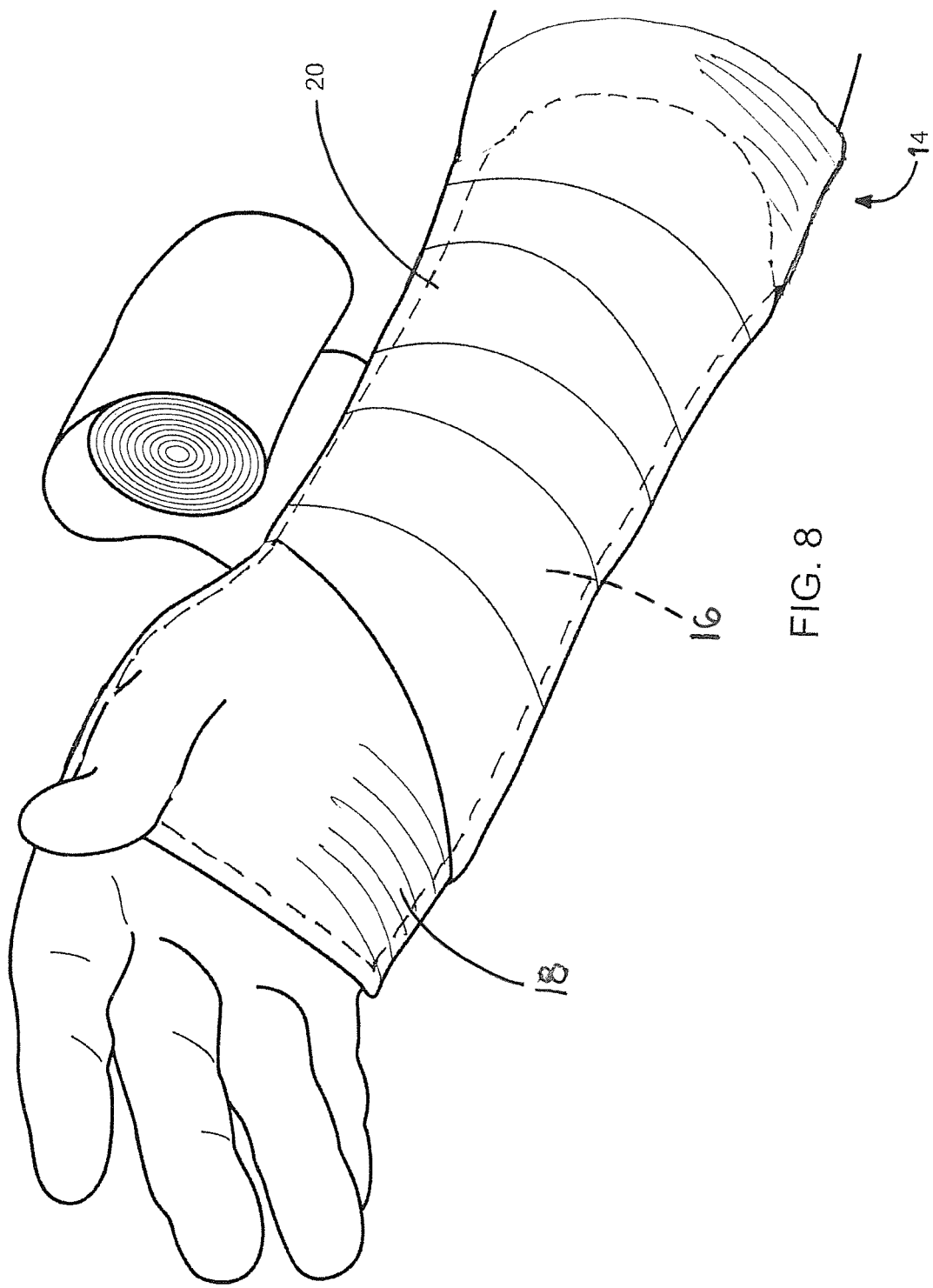
FIG. 8 shows the splint being overwrapped with an elastic bandage to hold the splint in its proper shape during hardening and to retain the splint on the arm.

Referring now to FIG. 7, the splint 14 is applied to the limb and carefully molded to achieve a close conformation to the limb. This includes carefully positioning the hand and wrist as needed, and forming a distal portion of the splint 14 under the hand. As shown in FIG. 8, the splint 14 is then overwrapped with a suitable wrapping, for example, an elastic bandage 20. The bandage 20 retains the splint 14 in its molded position against the limb during hardening, and thereafter maintains the splint 14 in its supporting position against the limb during that treatment phase.

The procedure described above is intended for use during the initial, acute, phase of treatment. When severe swelling is present, a hard plaster of Paris or synthetic cast may be placed on the limb after the swelling has subsided.

Figure 9:
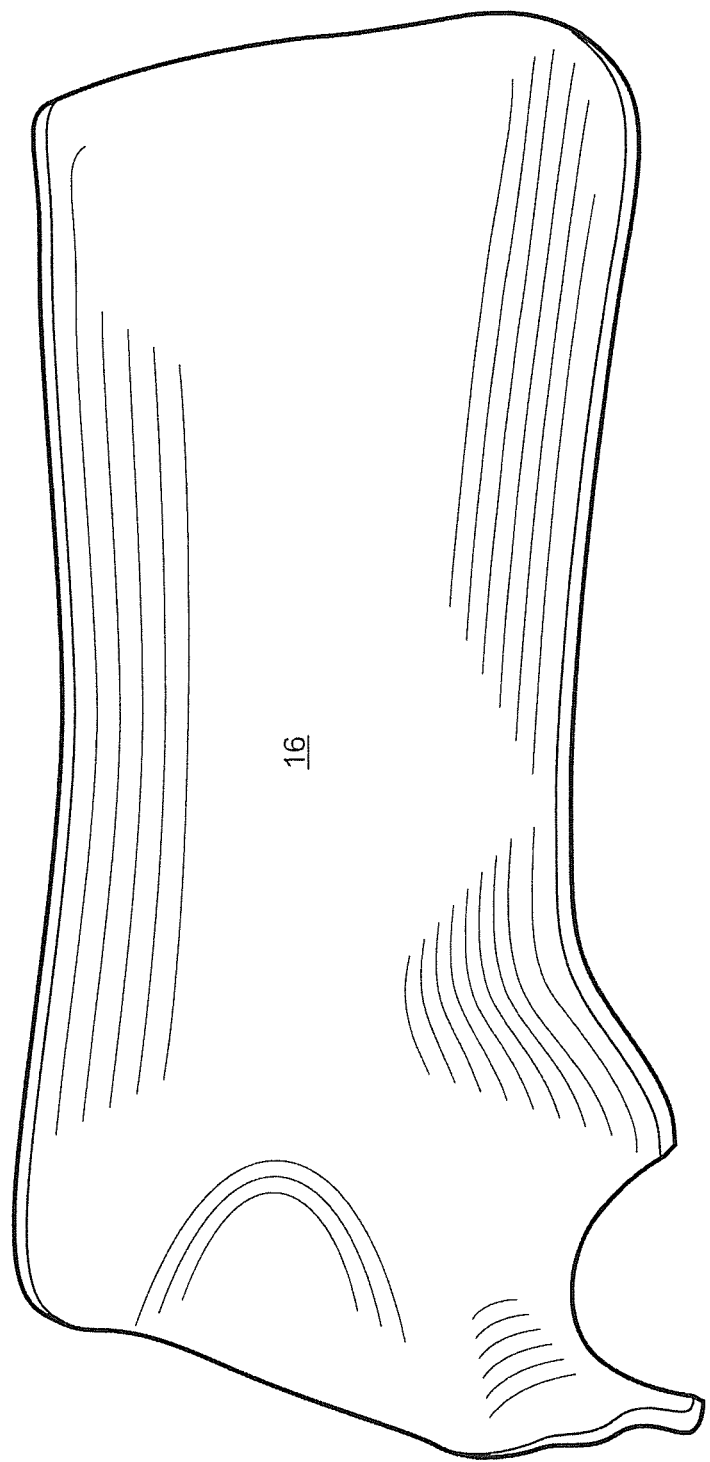
FIG. 9 shows the molded substrate after removal of the cover layer.

Whether or not a hard cast is applied, after the splint 14 is removed, it may later be reused in combination with a soft goods removable cast. As shown in FIG. 9, the cover 18 has been removed from the substrate 16, leaving only the bare substrate 16 for additional use. While it is preferable to remove the cover 18, this may not be required in all cases, the relevant issue being whether the substrate 16, with or without the cover 18, provides adequate support and conformation when used as described below.

Figure 10:
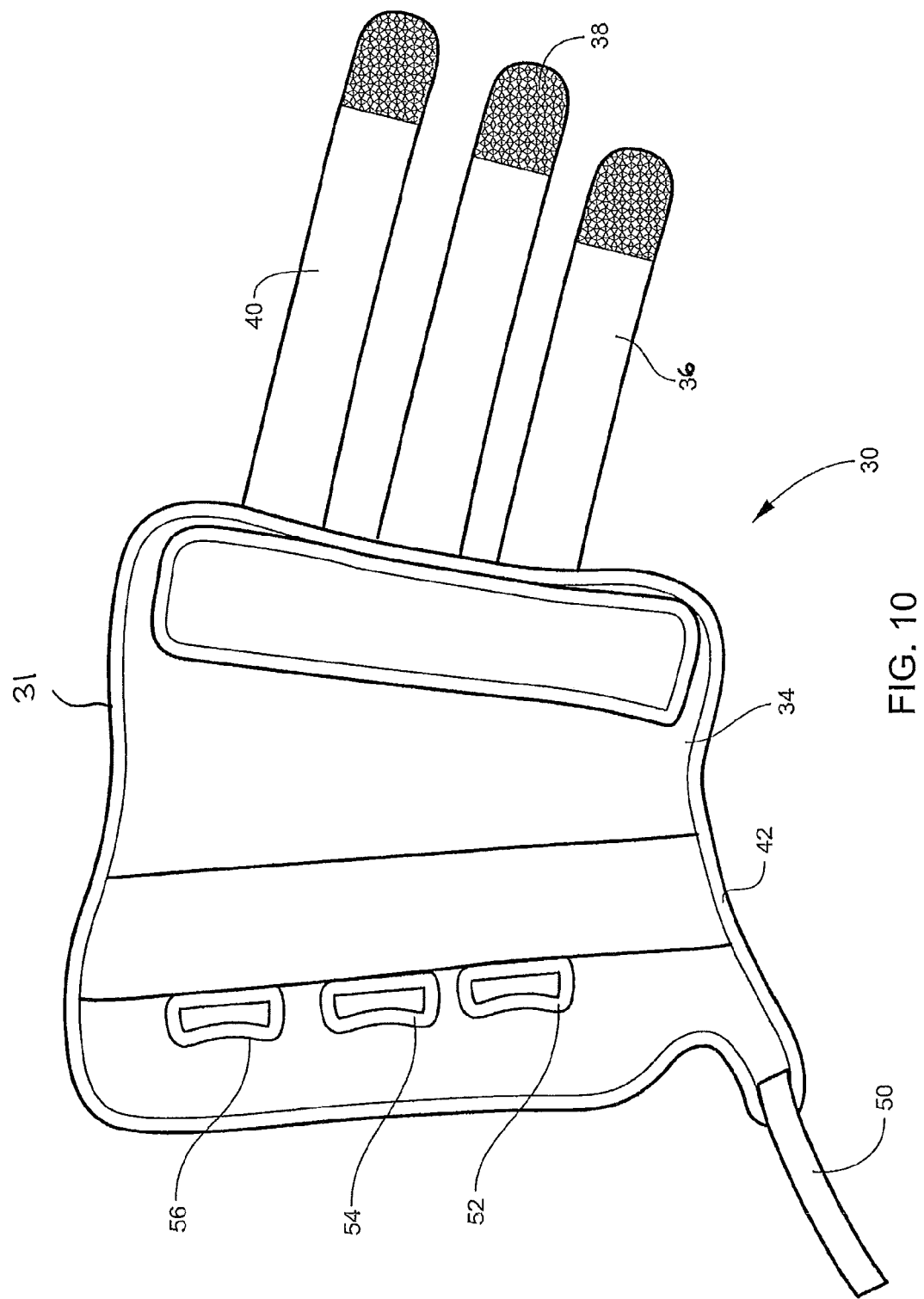
FIG. 10 is a view of the outer side of a soft goods removable cast according to a preferred embodiment of the invention.
Figure 11:
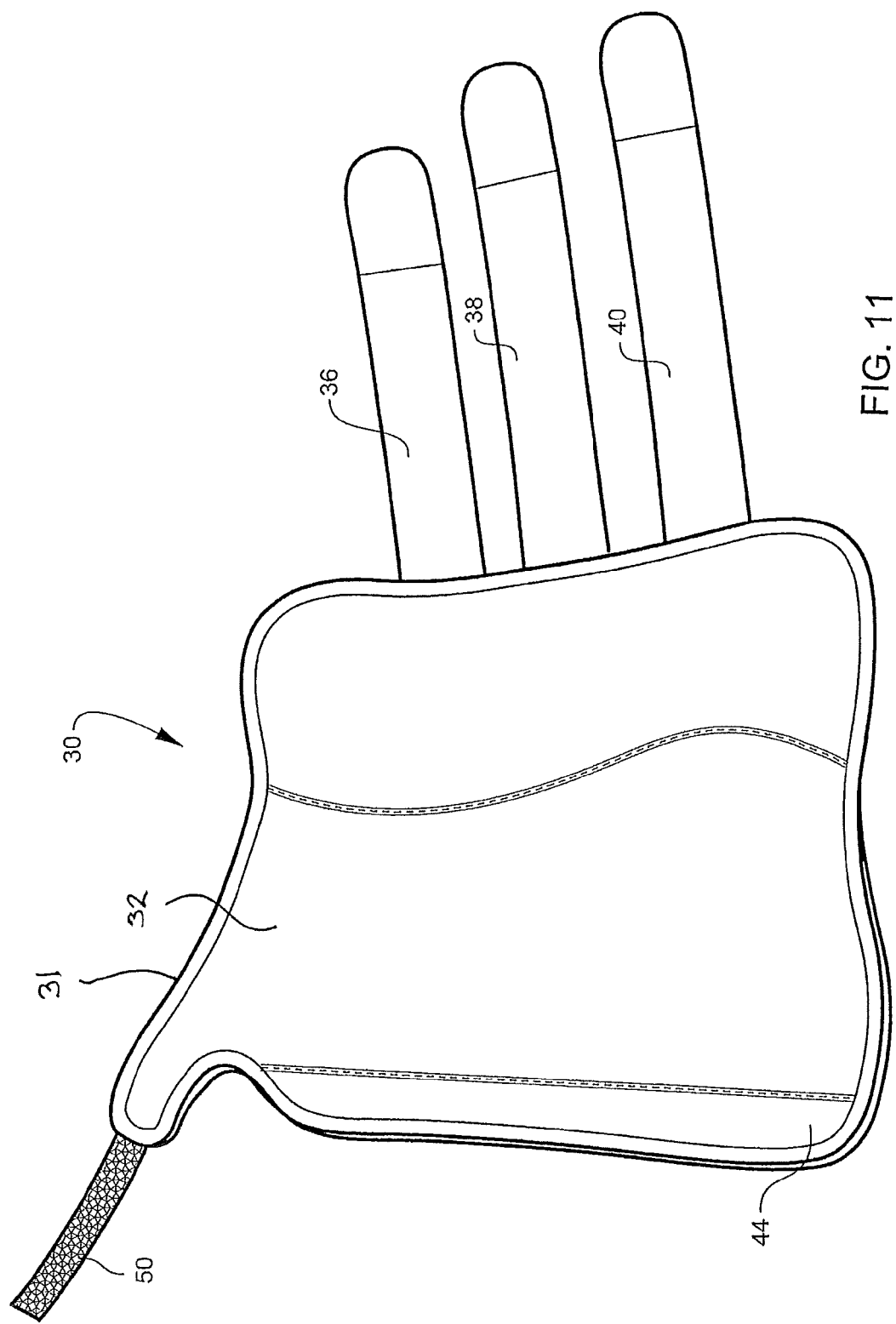
FIGS. 11-16 are sequential views showing insertion of the molded substrate into the soft goods cast and application of the cast to the forearm.
Figure 12:
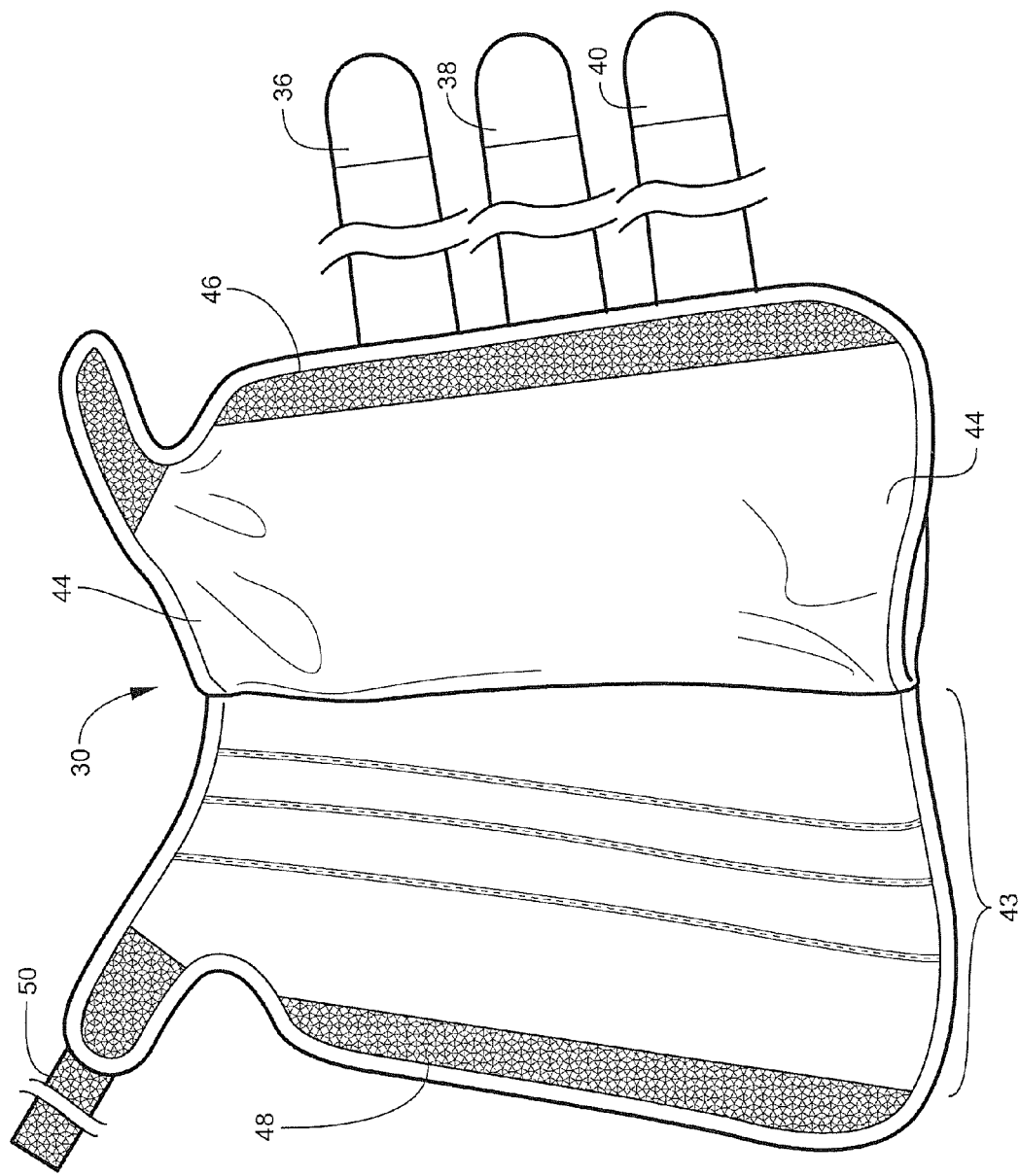

FIGS. 10 and 11 show opposite sides of a soft goods, removable cast 30 that is used in combination with the substrate 16 during post-acute and rehabilitation phases. The cast 30 includes a body 31 fabricated of a soft, conformable, stretch-knit material 32 on the interior, and an exterior fabric 34 with a loop surface for receiving complementary hooks carried by three securing straps 36, 38, 40 attached to the body 31. The interior fabric 32 and the exterior fabric 34 are bound together by an edge binding 42. The cast 30 has a light synthetic padding material sandwiched between the interior fabric 32 and the exterior fabric 34 in the bracketed area 43 in FIG. 12. The area 43 is the part of the cast 30 that directly engages the medial aspect of the arm and hand when the cast 30 is in place.

The interior of the cast 30 includes a fabric flap 44 seamed along one edge to the body 31. The flap 44 is movable between a closed position as shown in FIG. 11 and an open position shown in FIG. 12. The flap 44 includes a strip of loop material 46 fastened along its outer edge that releasably fastens to a complementary strip of hook material 48 fastened along an edge of the body 31, as shown. The cast 30 also includes an outwardly-extending hand strap 50 with a tab of hook material on the end that releasably engages the exterior loop surface of the exterior fabric 34 to close the cast 30 around the hand.

Three strap fastening rings 52, 54, 56 are attached to the exterior fabric 32 of the body 31 and cooperate with the straps 36, 38, 40, respectively, to secure the cast 30 around the forearm. The straps 36, 38, 40 are extended through respective strap fastening rings 52, 54, 56 and doubled over themselves, placing the hooks on the straps 36, 38, 40 in position to engage the exterior fabric 32.

Figure 13:
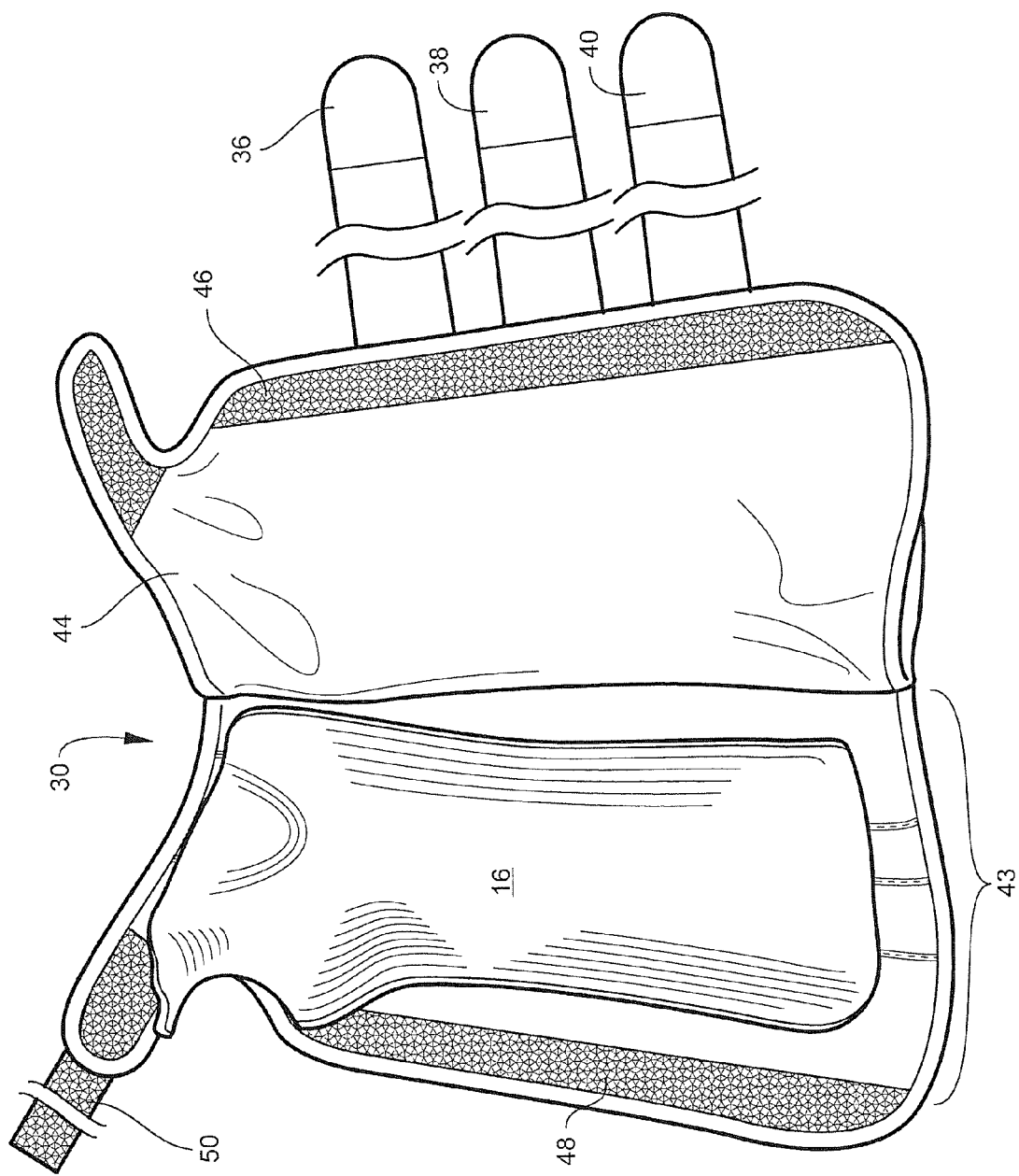
Figure 14:
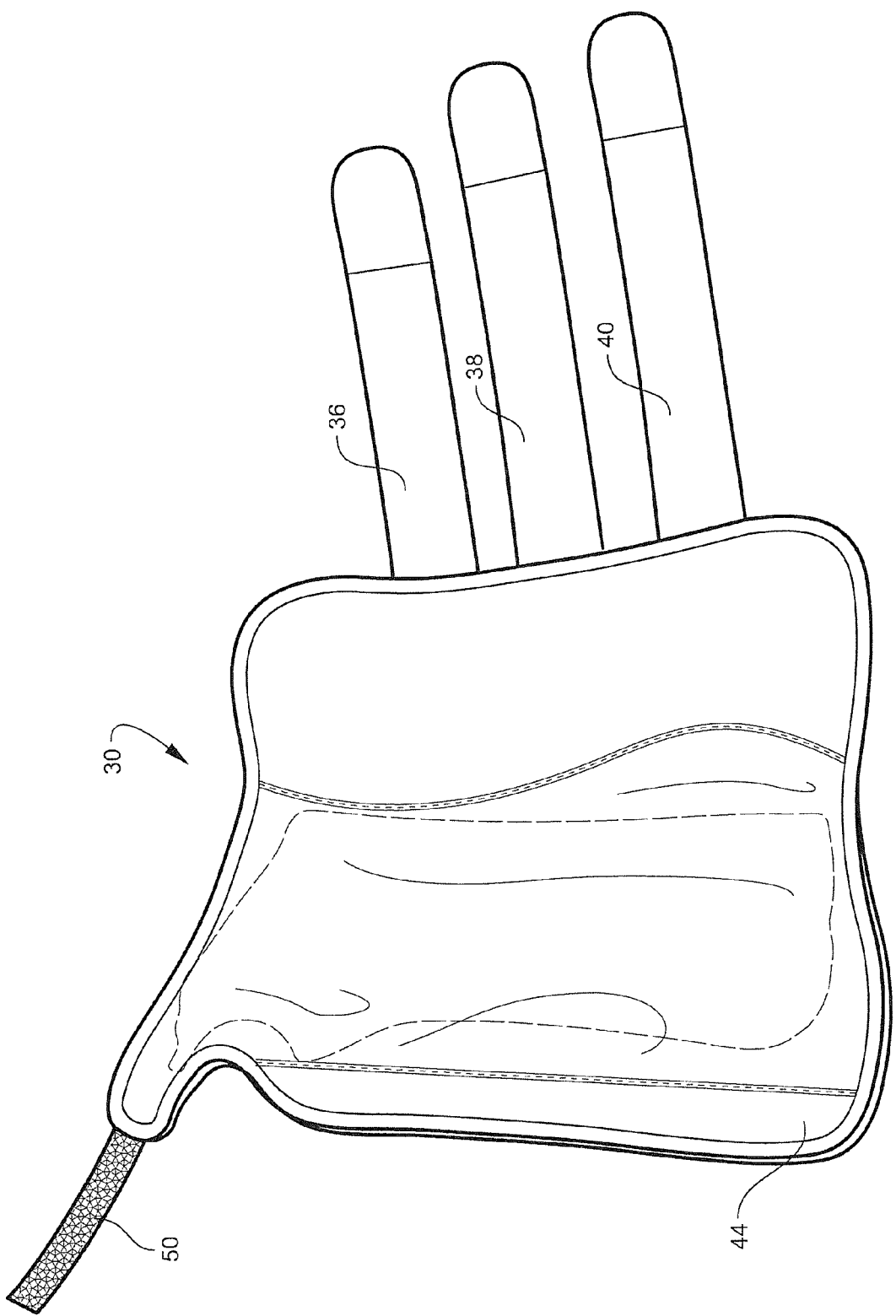
Figure 15:
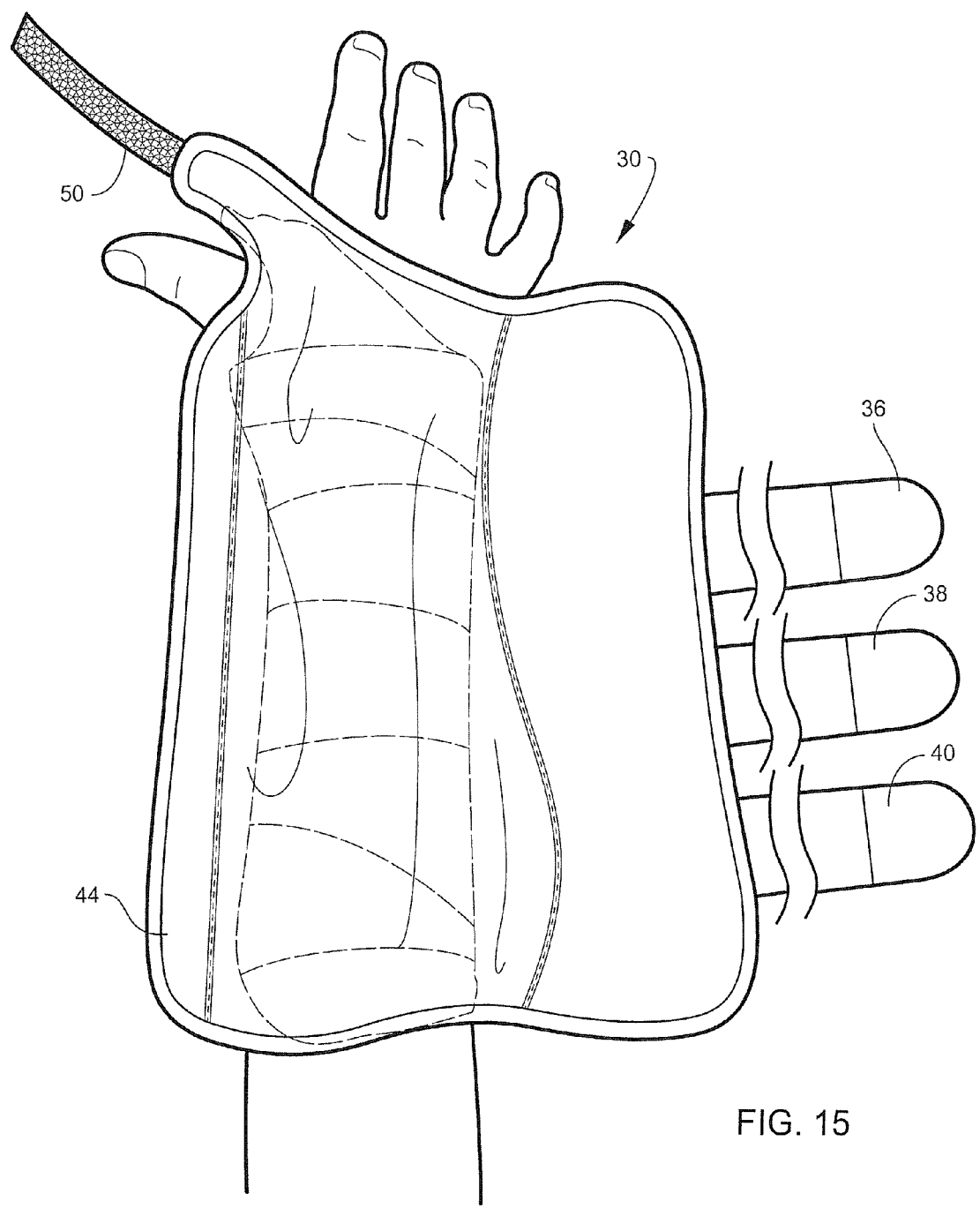
Figure 16:
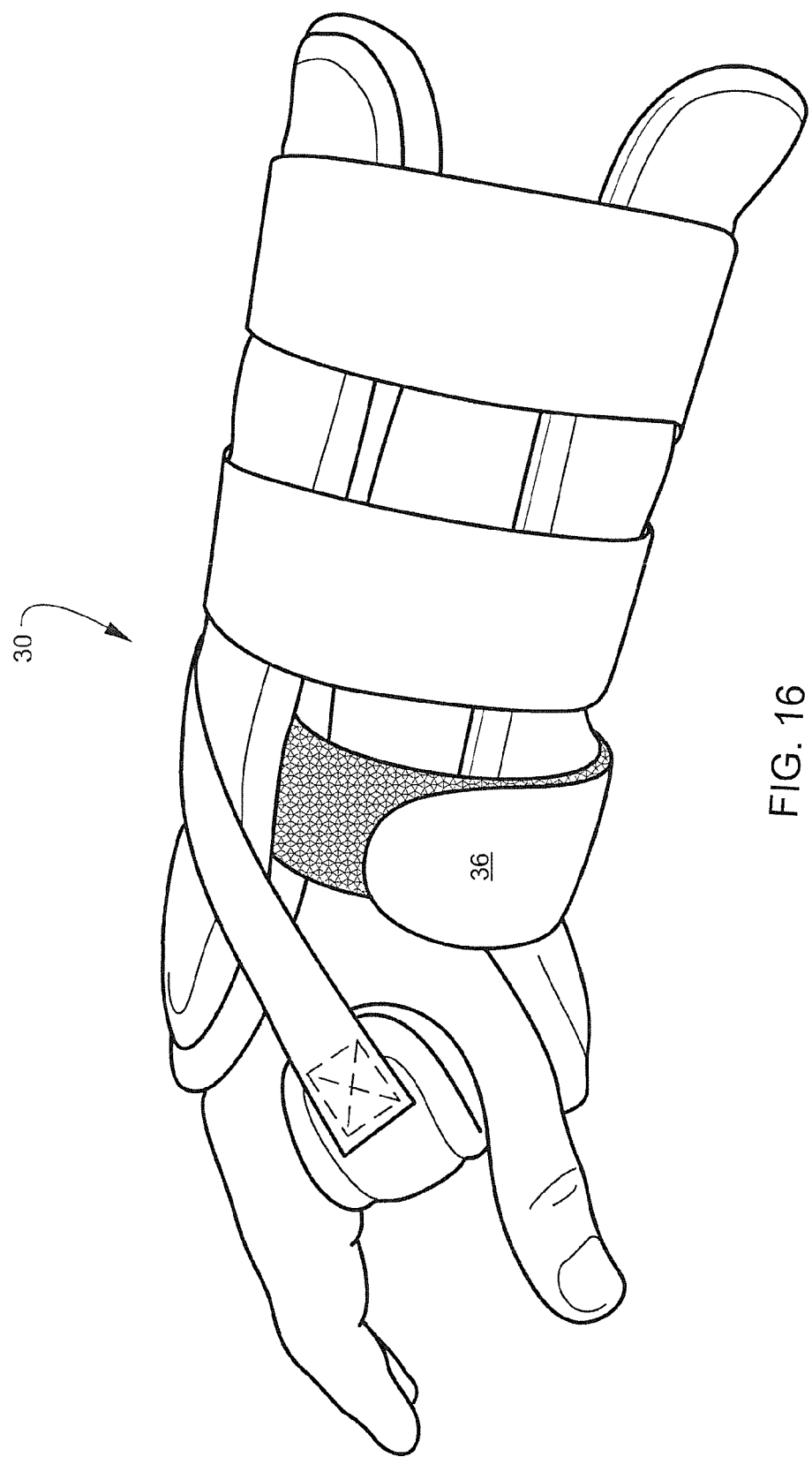

The cast 30 is prepared for use by taking the molded substrate 16, typically after removing the cover 18, and placing it in the interior of the cast 30 between the strip 46 of loop material and the strip 48 of hook material with the flap 44 in the open position, as shown in FIG. 13. The flap 44 is then folded into its closed position, FIG. 14, forming a protective pocket enclosing the substrate 16. The arm is placed over on onto the substrate 16, FIG. 15, and the cast 30 is folded around the arm and secured in place with the straps 36, 38, 40 and 50, as described above. The cast 30 provides continued support, but is easily removable and adjustable as needed during the remainder of the healing process. Because the original molded substrate 16 is reused, a proper fit is insured while avoiding the cost of supplying and applying another splint for use with the cast 30.

Figure 17:
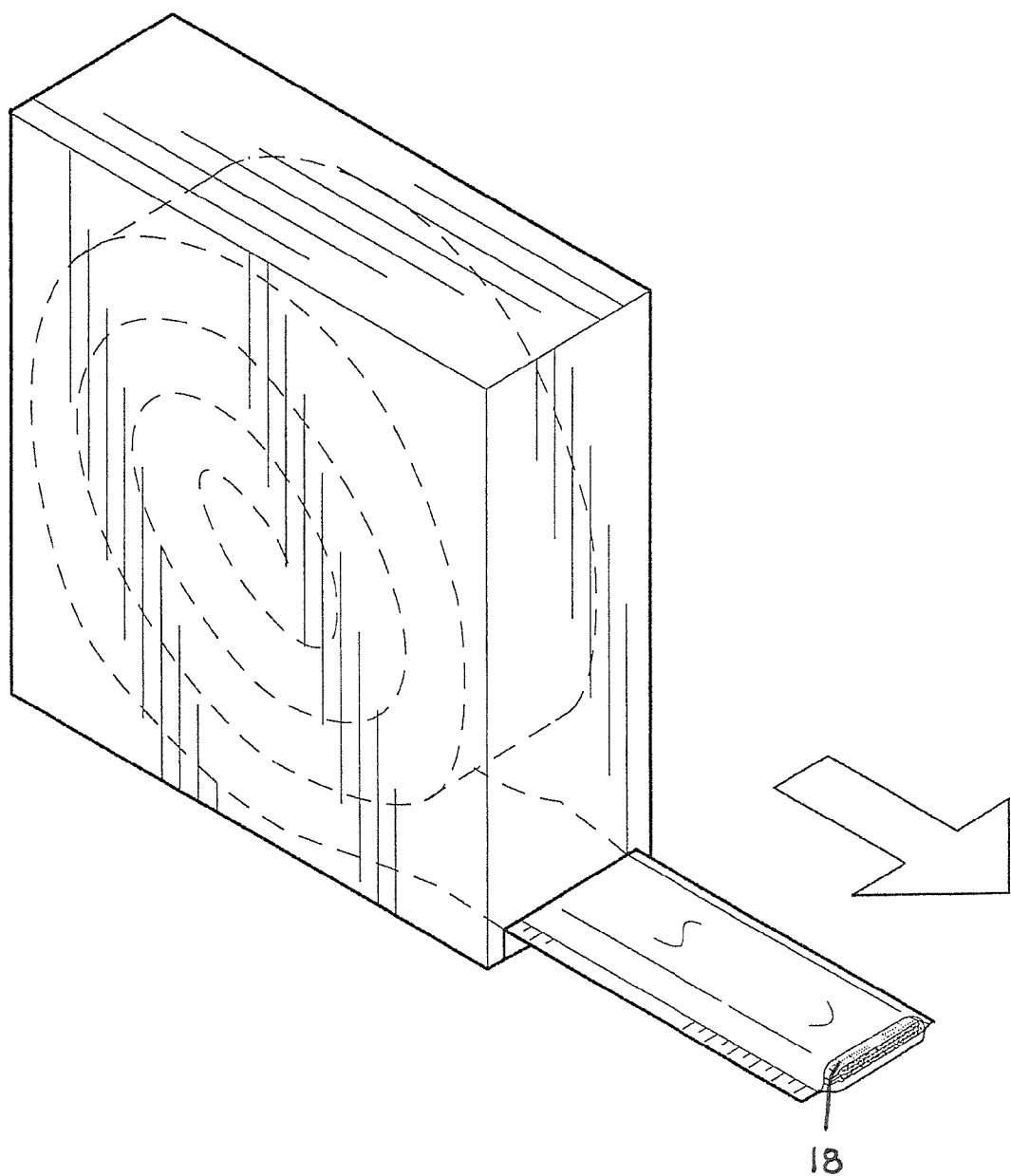
FIG. 17 illustrates a roll-form type of splint and packaging suitable for use in accordance with the invention.
Figure 18:
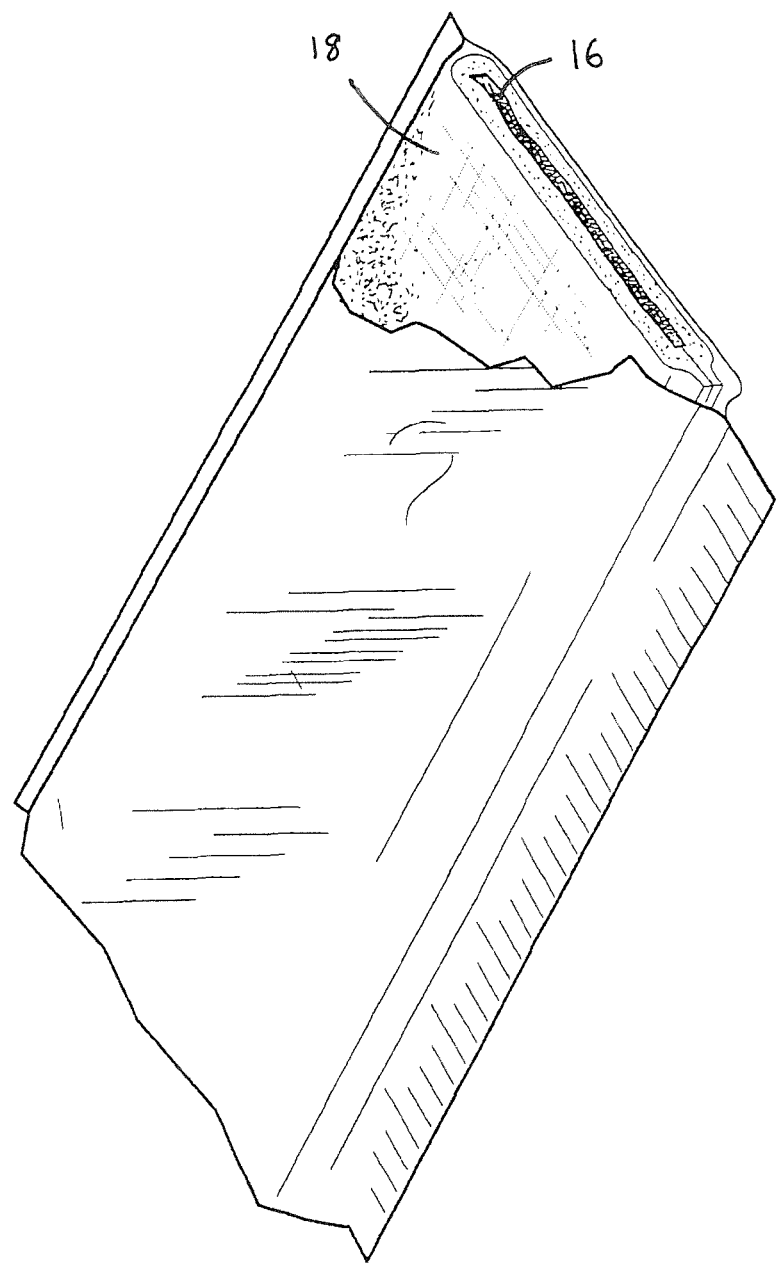
FIG. 18 illustrates a length of roll-form splint material removed from the coil of material shown in FIG. 17.

As shown in FIGS. 17 and 18, a roll-form type of splint material may be used as an alternative to the pre-cut splint 14 described above. This type of splint material is fully described in applicant's U.S. Pat. No. 4,770,299. As described above, the splint is prepared and applied to the patient as a splint during an acute phase of treatment. Thereafter, the cover surrounding the substrate is preferably removed, and the molded substrate is mated with the cast 30, also as described above.

A moldable injury therapy device and method is described above. Various details of the invention may be changed without departing from the scope of the invention. Furthermore, the foregoing description of the preferred embodiment of the invention and best mode for practicing the invention are provided for the purpose of illustration only and not for the purpose of limitation, the invention being defined by the claims.

What is claimed is:

1. A multi-phase orthopedic system, comprising:
   (a) a sleeve formed of moisture-impervious material and sealable to prevent entry of moisture;
   (b) a moldable splint positioned in the sleeve and sealed therein against entry of moisture until use, the splint comprising a substrate, a reactive system impregnated into or coated onto the substrate and remaining stable when maintained in substantially moisture-free conditions and hardening upon exposure to sufficient moisture to form a rigid, self supporting structure, and a removable cover enclosing the substrate along its length and forming a barrier between the substrate and a limb during an initial treatment phase during which the splint is worn by a patient on the limb;
   (c) an elongate removable wrap for retaining the splint on the limb; and
   (d) a removable cast for application to the limb during a subsequent treatment phase, and comprising:
      (1) a cast body having an interior side and exterior side;
      (2) a flap carried by the body and movable between an open position, and a closed position overlying a part of the cast body to be applied to a treatment area of the limb, the flap adapted to cover and retain between the cast body and the flap the splint worn by the patient during the initial treatment phase in the same position as the location of the splint during the initial treatment phase;
   wherein the removable cover is configured to be removed from the substrate prior to placing the moldable splint between the flap and the cast body.

2. A multi-phase orthopedic system according to claim 1, wherein the substrate is pre-formed into a shape suitable for application to a limb to be treated.

3. A multi-phase orthopedic system according to claim 1, wherein the removable cast includes a plurality of straps and complementary strap fastening rings for being releasably positioned around the cast for securing the cast to the limb.

4. A multi-phase orthopedic system according to claim 1, wherein the cast includes a padding layer positioned on the cast to overlie a part of the cast body to be applied to the treatment area of the limb.

5. A multi-phase orthopedic system according to claim 1, wherein the cast comprises a short arm cast adapted for being placed on a forearm of a patient, and includes a thumb recess portion positioned for receiving the thumb and a retention strap for retaining the thumb recess portion around the thumb.

6. A multi-phase orthopedic system according to claim 1, wherein the substrate comprises an elongate medical bandage material substantially the same length as the sleeve and positioned in the sleeve in a single length along length of the sleeve, and a seal for resealing the sleeve against entry of moisture after a predetermined length of the bandage material has been dispensed from the sleeve for use to prevent hardening of the substrate of the bandage material remaining in the sleeve.

7. A method of immobilizing a limb in multiple treatment phases, comprising the steps of:
   (a) providing:
      (i) a sleeve formed of moisture-impervious material and sealable to prevent entry of moisture;
      (ii) a splint positioned in the sleeve and sealed therein against entry of moisture until use, the splint comprising a substrate, a reactive system impregnated into or coated onto the substrate and remaining stable when maintained in substantially moisture-free conditions and hardening upon exposure to sufficient moisture to form a rigid, self supporting structure, and a cover enclosing the substrate along its length and forming a barrier between the substrate and a limb during an initial treatment phase during which the splint is worn by a patient on the limb;
      (iii) an elongate removable wrap for retaining the splint on the limb; and
      (iv) a removable cast for application to the limb, and comprising a cast body having an interior side and exterior side, and a flap carried by the body and movable between an open position, and a closed position overlying a part of the cast body to be applied to a treatment area of the limb, the flap adapted to cover and retain the splint between the cast body and the flap;
   (b) removing the splint from the sleeve and wetting the splint;
   (c) molding the splint to the limb;
   (d) securing the splint in its molded position to the limb for being worn during an initial orthopedic treatment phase;
   (e) removing the splint from the limb;
   (f) removing the cover from the substrate;
   (g) placing the splint between the flap and the cast body of the cast; and
   (h) releasably applying the cast and the splint to the limb for being worn during a subsequent orthopedic treatment phase; removing the cover from the substrate before placing the splint between the flap and the cast body of the cast.

8. A method according to claim 7, and including the step of pre-forming the substrate into a shape suitable for application to a limb to be treated.

9. A method according to claim 7, and including the step of providing an elongate medical bandage material substantially the same length as the sleeve and positioned in the sleeve in a single length along the length of the sleeve, and a seal for resealing the sleeve against entry of moisture after a predetermined length of the bandage material has been dispensed from the sleeve for use to prevent hardening of the substrate of the bandage material remaining in the sleeve.

* * * * *